(12) United States Patent
Cao et al.

(10) Patent No.: US 8,178,741 B2
(45) Date of Patent: May 15, 2012

(54) METHOD AND APPARATUS FOR REGENERATING CATALYST DURING OXYGENATES TO OLEFINS REACTION

(75) Inventors: Chunshe J. Cao, Houston, TX (US); James H. Beech, Jr., Kingwood, TX (US); Michael P. Nicoletti, Houston, TX (US); Thomas H. Colle, Houston, TX (US); Teng Xu, Hampton, NJ (US); Stephen N. Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 74 days.

(21) Appl. No.: 12/793,340

(22) Filed: Jun. 3, 2010

(65) Prior Publication Data

US 2011/0021857 A1    Jan. 27, 2011

Related U.S. Application Data

(60) Provisional application No. 61/227,287, filed on Jul. 21, 2009.

(51) Int. Cl.
*C07C 1/00* (2006.01)
*B01J 20/34* (2006.01)
*B01J 19/00* (2006.01)

(52) U.S. Cl. ........ 585/640; 585/501; 585/638; 585/639; 585/809; 502/56; 422/187; 422/198

(58) Field of Classification Search ............... 585/501, 585/638, 639, 640, 809; 502/156; 422/187, 422/198
See application file for complete search history.

(56) References Cited

U.S. PATENT DOCUMENTS

| | | | |
|---|---|---|---|
| 6,448,460 B2 * | 9/2002 | Janssen et al. | 585/638 |
| 2006/0217582 A1 * | 9/2006 | Xu et al. | 585/639 |

FOREIGN PATENT DOCUMENTS

| | | |
|---|---|---|
| EP | 1 257 359 | 11/2002 |
| WO | 2007/021382 | 2/2007 |

* cited by examiner

*Primary Examiner* — Prem C Singh
(74) *Attorney, Agent, or Firm* — Kevin M. Faulkner; Ronald M. Pols

(57) ABSTRACT

Disclosed herein is a method of recovery of the activity of a molecular sieve catalyst following use of the catalyst in an OTO conversion process. This is achieved by a regeneration apparatus and a method of regenerating a molecular sieve catalyst, comprising two stages. In a pretreatment stage, the catalyst is pretreated under pretreatment conditions by heating the catalyst to a temperature of between 320° C. to 700° C. in an oxygen depleted medium for a residence time of between 1 minute to two hours; and, in a regeneration stage, the catalyst is regenerated under regeneration conditions by heating the catalyst at a temperature of between 200° C. to 700° C. in an oxidizing medium for a residence time of between 1 to 60 minutes.

12 Claims, 7 Drawing Sheets

METHOD AND APPARATUS FOR REGENERATING CATALYST DURING OXYGENATES TO OLEFINS REACTION

CROSS-REFERENCE TO RELATED APPLICATION

The present claims priority to Provisional U.S. Patent Application No. 61/227,287 filed Jul. 21, 2009, all of which is incorporated by reference.

FIELD OF THE INVENTION

The present disclosure relates to regenerating catalyst. More particularly, the disclosure relates to controlling the activity and/or catalyst life time of the catalyst following regeneration.

BACKGROUND OF THE INVENTION

Light or prime olefins, defined herein as ethylene and propylene, serve as feeds for the production of numerous chemicals. Olefins traditionally are produced by petroleum cracking. Because of the limited supply and/or the high cost of petroleum sources, the cost of producing olefins from petroleum sources has increased steadily.

Alternative feedstocks for the production of light olefins are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The conversion of oxygenates to olefins (OTO), particularly the conversion of methanol to olefins (MTO), in a hydrocarbon conversion apparatus generates and deposits carbonaceous material (coke) on the molecular sieve catalysts used to catalyze the conversion process. Excessive accumulation of these carbonaceous deposits interferes with the catalyst's ability to promote the reaction and reduces catalyst life. In order to avoid unwanted build-up of coke on molecular sieve catalysts, the OTO process incorporates a second step comprising catalyst regeneration. During regeneration, the coke is at least partially removed from the catalyst by combustion with oxygen, which restores the catalytic activity of the catalyst and forms a regenerated catalyst. The regenerated catalyst then may be reused to catalyze the conversion of methanol to olefins.

In conventional regeneration vessels, coked catalyst is directed from a reactor to a catalyst regenerator. In a catalyst regenerator, a regeneration medium, usually containing oxygen in at least a stoichiometric amount, enters the regenerator, and coke is removed from the coked catalyst by combustion with the regeneration medium to form regenerated catalyst and gaseous byproducts. The bulk of the regenerated catalyst from the regenerator is returned to the reactor. The gaseous byproducts are forced out an exhaust outlet oriented in the upper section of the catalyst regenerator.

The combustion of the carbonaceous deposits from molecular sieve catalyst compositions during catalyst regeneration is an exothermic process which takes place at high temperatures of typically 650° C. and more. The exothermic nature of catalyst regeneration presents a problem in OTO regeneration systems because the amount of coke formed on the molecular sieve catalyst compositions utilized in OTO reaction systems is preferably maintained at higher levels than in conventional FCC processes in order to maintain a high prime olefin selectivity (POS). "POS" is defined as the amount in grams (g) of ethylene and propylene produced per gram of MeOH (excluding $H_2O$) multiplied by 100%.

For example, EP 1 257 359 A indicates that some level of coking, thought to be the presence of single ring aromatics and methylated naphthalenes within the cages of the molecular sieve catalyst, is beneficial for the prime olefin selectivity of the catalyst, to allow the solid acid of the sieve to become active, and selective for making light olefins.

Conventional regeneration by the complete oxidation of the coke in air at high temperatures in a regenerator removes all hydrocarbon species remaining in/on the catalyst sieve, including the single ring aromatics. This reduces the catalytic activity and selectivity for producing light olefins and also reduces catalyst life.

WO 2007/021382 discloses conventional regeneration in a single stage regeneration process.

The present disclosure aims to obviate or at least mitigate the above described problem and/or to provide improvements generally.

SUMMARY OF THE INVENTION

Accordingly, disclosed herein is a process, an apparatus and an OTO unit as defined in any of the accompanying claims.

In an embodiment, there is provided a method for regenerating a molecular sieve catalyst for converting oxygenates into olefins, comprising:

a) in a pretreatment stage, pretreating a molecular sieve catalyst under pretreatment conditions by heating the catalyst to a pretreatment temperature of between 320° C. to 700° C. in an oxygen depleted medium for a residence time of between 1 minute to 2 hours, preferably between 1 minute to 1 hour; and b) in a regeneration stage, regenerating the catalyst under regeneration conditions by heating the catalyst at a regeneration temperature of between 200° C. to 700° C. in an oxidizing medium for a residence time of between 1 minute to 2 hours, preferably 1 minute to 30 minutes.

The method provides a regenerated catalyst with improved prime olefin selectivity (POS) and catalyst life in comparison to catalyst which is regenerated in a single stage without pretreatment. Additionally, the process provides regeneration of heavily coked catalyst while maintaining desirable temperature characteristics during the regeneration process. The regenerated catalyst described herein also has an improved catalyst life when treated as described.

In another embodiment, there is provided a catalyst regeneration apparatus for an oxygenates into olefins conversion process, comprising:

a) a catalyst pretreater for pretreating a molecular sieve catalyst under pretreatment conditions, said conditions comprising a temperature of between 320° C. to 700° C. in an oxygen depleted medium and a residence time of between 1 minute to 2 hours, preferably between 1 minute to 1 hour; and b) a regenerator for regenerating the catalyst in an oxidizing medium under regeneration conditions, said regeneration conditions comprising a temperature of between 200° C. to 700° C. and a residence time of between 1 minute to 2 hours, preferably 1 minute to 30 minutes.

This apparatus produces a regenerated catalyst of a similar activity and selectivity as fresh catalyst. Therefore, this unit greatly enhances the efficiency of the oxygenates to olefins process.

In a further embodiment, there is provided a method of regenerating a molecular sieve catalyst for converting oxygenates into olefins, comprising in a single regeneration stage, regenerating the catalyst under regeneration conditions by heating the catalyst at a regeneration temperature of between 300° C. to 480° C. in an oxidizing medium for a regeneration residence time of between 1 minute to 2 hours, preferably between 1 minute to 1 hour, and more preferably between 1 to 30 minutes.

This process results in a catalyst having favorable activity and catalyst life in comparison to a catalyst which is regenerated at a higher temperature.

In another embodiment, there is provided a method for converting oxygenates into olefins by means of molecular sieve catalyst comprising in a reaction stage, reacting the catalyst with the oxygenates under reaction conditions, the reaction conditions comprising a reaction temperature from 250° C. to 700° C., a pressure of 5 kPaa to 1 MPaa and a weight hourly space velocity of at least 1 $hr^{-1}$; regenerating at least a portion of the catalyst from the reaction stage; and, following regeneration, returning the catalyst to the reaction stage.

Finally, there is provided an oxygenates-to-olefins ("OTO") conversion unit comprising a reactor, a catalyst separator and a regeneration apparatus. In the unit, the catalyst reacts in the reactor with the oxygenates under reaction conditions, the reaction conditions comprising a reaction temperature from 250° C. to 700° C., a pressure of 5 kPaa to 1 MPaa and a weight hourly space velocity of at least 1 $hr^{-1}$; the regeneration apparatus regenerating at least a portion of the catalyst from the reactor; and the regeneration apparatus returning the catalyst following regeneration to the reactor.

DETAILED DESCRIPTION OF THE EMBODIMENTS

Figure 1A:
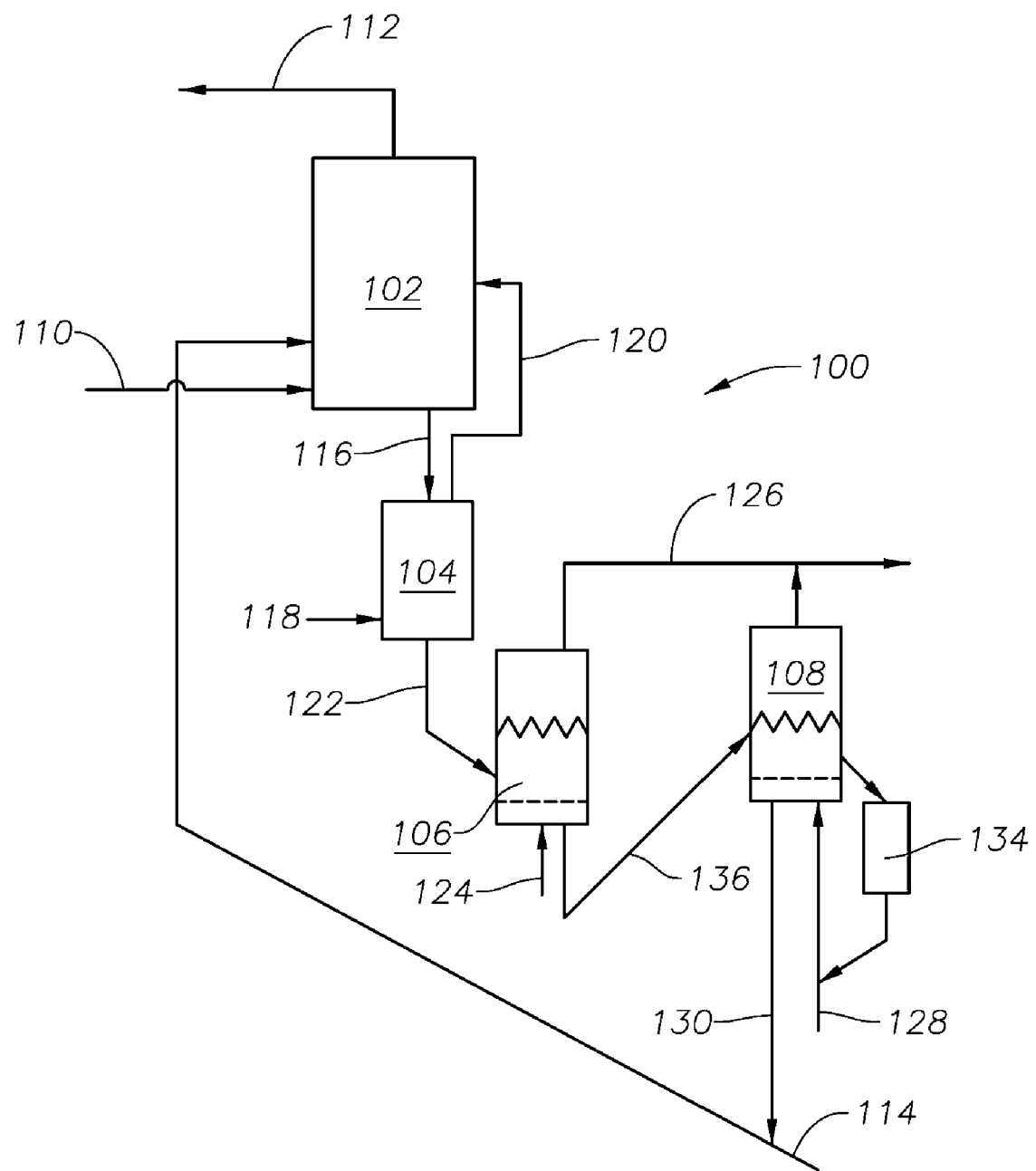
FIG. 1a shows a diagrammatic layout of an OTO conversion process according to an embodiment.

Oxygenates to olefins conversion reactions involve contacting an oxygenate feedstock with a formulated molecular sieve catalyst. As the reaction proceeds, a carbonaceous material (coke) builds up on the molecular sieve catalyst. A low level of carbonaceous deposits, of between 0.5% to 10%, typically 2% to 7% by weight based on the overall weight of the catalyst, improves the selectivity for light olefins in comparison with fresh catalyst. However, higher levels of carbonaceous deposits reduce the selectivity and life time of the catalyst. To control the build up of carbonaceous deposits on the catalyst, the catalyst is conventionally regenerated in a regenerator whereby the carbonaceous deposits are removed by oxidation of the carbonaceous material.

In conventional regenerators, coke is partially removed from the spent catalyst in a single stage. We have found that the performance of the catalyst following regeneration cannot be completely restored in comparison with the fresh activity of the catalyst, even when the regenerator is operated in full burn mode and most of the coke is removed from the catalyst. Catalytic activity decreases significantly after the first cycle of regeneration. Furthermore, the activity of the regenerated catalyst is independent of the coke amount which was initially present on the catalyst.

One objective of the process described herein is to improve the recovery of the activity of the catalyst following use of the catalyst in a OTO conversion process.

In an embodiment, this objective is achieved by a method of regenerating a molecular sieve catalyst, comprising two stages. In a pretreatment stage, the catalyst is pretreated under pretreatment conditions by heating the catalyst to a temperature of between 320° C. to 700° C. in an oxygen depleted medium for a residence time of between 1 minute to 1 hour, preferably between 10 to 50 minutes, and; in a regeneration stage, the catalyst is regenerated under regeneration conditions by heating the catalyst at a temperature of between 200° C. to 700° C. in an oxidizing medium for a residence time of between 1 to 60 minutes, preferably between 10 to 50 minutes.

Regenerated catalyst of this process showed catalyst activity and selectivity which was similar to fresh catalyst.

Preferably, all of the pretreated catalyst is regenerated. Alternatively, a portion of the pretreated catalyst is returned to the oxygenate to olefins reactor without being regenerated. In this way, a desired coke content on the overall quantity of catalyst in the reactor can be achieved.

The process may be implemented in a catalyst regeneration apparatus or a unit for an oxygenates into olefins (oxygenates-to-olefins, or "OTO") conversion process. The apparatus may comprise a) a catalyst pretreater for pretreating the catalyst under pretreatment conditions, said conditions comprising a temperature of between 320° C. to 700° C. in an oxygen depleted medium and a residence time of between 1 minute to 1 hour, preferably between 10 to 50 minutes; and b) a regenerator for regenerating the catalyst in an oxidizing medium under regeneration conditions, said regeneration conditions comprising a temperature of between 200° C. to 700° C. and a residence time of between 1 to 60 minutes, preferably between 10 to 50 minutes.

In particular, the apparatus is adapted to react in a reaction stage, the catalyst with the oxygenates under reaction conditions, the reaction conditions comprising a reaction temperature from 250° C. to 700° C., a pressure of 5 kPaa to 1 MPaa and a weight hourly space velocity of at least 1 $hr^{-1}$. At least a portion of the catalyst from the reaction stage is pretreated and regenerated as herein before described and the catalyst is returned to the reaction stage. At least a portion of the catalyst may be returned to the reaction stage following pretreatment in the pretreatment stage without being regenerated to provide catalyst in the reactor which has a desired coke content.

We will now discuss the catalyst pretreatment and the catalyst regeneration stages in further detail below.

Pretreatment

The pretreatment of the catalyst may be described as being performed within the range of from 320° C. to 400 or 500 or 600 or 700° C. in certain embodiments. In other embodiments, the pretreatment may be described as being performed in two stages. For example, during pretreatment the catalyst may be heated at a first pretreatment temperature for a first residence time followed by increasing the pretreatment temperature to a second temperature and maintaining the second temperature for a second residence time.

The first pretreatment temperature may be within the range from 320 to 480° C. in one embodiment, and from 320 to 400° C. in another embodiment, and from 350 to 400° C. in yet another embodiment, and from 350 to 480° C. in yet another embodiment. The temperature in the pretreatment stage may be increased from the first temperature to the second temperature at a rate of between 5° C. to 50° C. per minute, preferably between 10° C. to 30° C. per minute, more preferably between 15° C. to 25° C. per minute.

The second pretreatment temperature may be between 400° C. to 700° C., preferably between 450° C. to 660° C., most preferably between 550° C. to 660° C.

We have found that pretreatment which comprises heat up of the sieve at a first temperature of 320° C. or more and maintaining the temperature at this level for a period of time during a first residence time, followed by heating the sieve at a higher second temperature for a second residence time, is beneficial to arrive at a catalyst following regeneration which has similar activity to fresh catalyst. The first residence time may be between 0 to 100 minutes, preferably between 1 to 60 minutes, more preferably between 5 to 30 minutes. A residence time of 0 minutes means that no pretreatment takes place. The second residence time may be between 1 to 60 minutes, preferably between 5 to 30 minutes, and more preferably between 5 to 15 minutes. The second temperature may be identical to the temperature of the regeneration stage.

The pressure at the pretreatment stage may be in the range of from 5 psig (69 kPaa) to 60 psig (828 kPaa). Preferably, the regeneration pressure is at least 15 psig (207 kPaa), or at least 20 psig (242 kPaa), or at least 25 psig (275 kPaa). Preferably, the regeneration pressure is 30 psig (414 kPaa) or less. The pretreater may be operated as a fluidized bed. Preferably, the flow of the pretreatment medium is low so that the solids are minimally fluidized in the pretreatment medium. Typically, the superficial velocity is 0.01 m/s or more, preferably between 0.01 to 5 m/s, more preferably between 0.03 to 1 m/s to ensure adequate fluidization of the catalyst particles in the flow of the pretreatment medium.

In an embodiment, the catalyst in the pretreatment stage is heated by combustion of coke on the catalyst. Preferably, the coke is partially combusted to provide the heat in the pretreatment stage so that coke is retained on the catalyst. The pretreater may comprise combustion means for combusting coke on the catalyst to heat the catalyst in the pretreatment stage. In this way, the catalyst may be heated in an efficient way. Alternatively, as discussed in further detail below, the oxygen depleted medium may have a low concentration of oxygen to allow limited combustion of the coke on the catalyst to increase the temperature in the pretreatment stage to the desired value.

In another embodiment, the catalyst in the pretreatment stage is heated by mixing the catalyst in the pretreatment stage with catalyst from the regeneration stage. As the temperature of the catalyst in the regeneration stage is higher than the temperature of the catalyst in the pretreatment stage, the catalyst can be heated effectively. Also, as the regenerated catalyst is released in an oxygen depleted medium, this does not affect the activity of the regenerated catalyst. The pretreater may comprise a feed stream of catalyst from the regenerator to heat the catalyst in the pretreatment stage.

In the context of this disclosure, "oxygen depleted medium" refers to a pretreatment medium which does not significantly affect the weight percent (wt %) of coke on the catalyst during pretreatment. The pretreatment medium comprises no or limited concentrations of oxygen. Preferably, the oxygen depleted medium comprises less than 30%, preferably 20% of less, and most preferably 15% or less, of the stoichiometric amount of oxygen for completely removing coke from the catalyst. This prevents complete removal of carbonaceous deposits from the catalyst during the pretreatment stage. The oxygen depleted medium may also comprise an inert gas.

The pretreater may be integrated within a regenerator or, alternatively, the pretreater and regenerator may be separate. Gaseous effluent from the pretreater may be fed to the regenerator.

In a preferred embodiment, the pretreater has certain design parameters that facilitate the pretreatment of the catalyst particles, in addition to providing desirable flow characteristics for increasing entrained catalyst retention. The catalyst pretreater can be similar in lay-out to a regenerator. It may include a pretreatment zone into which a pretreatment medium and an at least partially coked catalyst from a reactor are fed. It may also include a separation zone to separate the catalyst from the oxygen depleted medium. The catalyst pretreater may also include a catalyst return into which pretreated catalyst can be fed from the pretreatment zone and from which the pretreated catalyst can be directed to the regenerator.

In an alternative embodiment, the catalyst pretreater and the catalyst regenerator are the same apparatus which is alternately operated as a pretreater and a regenerator by varying the medium between an oxygen depleted pretreatment medium and an oxygen containing regeneration medium under the herein described respective pretreatment and regeneration conditions.

Regeneration

In the regeneration stage, the catalyst is regenerated in an oxidizing medium at regeneration temperatures within the range of from 200 or 300 or 350 or 400° C. to 450 or 480 or 500 or 700° C. in certain embodiments.

In one embodiment, the regeneration pressure may be in the range of from 5 psig (69 kPaa) to 60 psig (828 kPaa). Preferably, the regeneration pressure is at least 15 psig (207 kPaa), or at least 20 psig (242 kPaa), or at least 25 psig (275 kPaa). Preferably, the regeneration pressure is 30 psig (414 kPaa) or less. The precise regeneration pressure is generally dictated by the pressure in the reaction system. Higher pressures are typically preferred for lowering equipment size and catalyst inventory; however, higher pressures also increase air blower power and cost. Nevertheless, the regeneration pressure may additionally or alternately be in the range from 30 psig (414 kPaa) to 150 psig (2.08 MPaa), for example from 45 psig (621 kPaa) to 120 psig (1.65 MPaa) or from 60 psig (828 kPaa) to 120 psig (1.65 MPaa).

The regenerator may be operated as a fluidized bed. Preferably, the flow of the regeneration medium is therefore at a superficial velocity of greater than 0.1 m/s, more preferably greater than 1.0 m/s to ensure adequate fluidization of the catalyst particles in the flow of the regeneration medium.

In another embodiment, the residence time (or catalyst holdup) of the catalyst in the regenerator is at least 10 minutes, or at least 15 minutes, or at least 20 minutes. Alternatively, the residence time in the regenerator can be 30 minutes or less, or 25 minutes or less.

Regeneration is preferably conducted at temperatures that are designed to effectively remove coke in an industrially practical amount of time while reducing the likelihood of catalyst damage or degradation.

Suitable regeneration conditions are those capable of burning coke from the coked catalyst composition to a desired level. Coke levels on the catalyst composition are measured by withdrawing the catalyst composition from the conversion process and determining its carbon content. In an embodiment, an increased level of coke remains on the catalyst after regeneration. Maintaining a higher level of coke both reduces the required regeneration time for catalyst to reach a desired coke level and increases the coke burning rate. Preferably, the regeneration conditions remove coke to less than 1.0 wt % based on the total weight of the coked molecular sieve catalyst composition entering the regeneration system, and more preferably to less than 0.75 wt %. Preferably, the regeneration conditions allow 0.3 wt % or greater of coke to remain on the catalyst relative to the total weight of catalyst after regeneration, or at least 0.4 wt %, or at least 0.5 wt %, or at least 0.6 wt %.

In another embodiment, the regeneration conditions can allow 0.1 wt % or greater of coke to remain on the catalyst relative to the total weight of catalyst after regeneration, or 0.2 wt % or greater. Allowing at least 0.1 wt % or greater of coke to remain on the catalyst, preferably greater than 0.2 wt %, and more preferably greater than 0.3 wt %, can allow for improved circulation between the regenerator and the reactor. The weight of coke on catalyst can be alternatively expressed in terms of the amount of molecular sieve present within the catalyst. The weight of molecular sieve within a catalyst will be a fraction of the total catalyst weight. The wt % of coke relative to the weight of molecular sieve can be determined by starting with the wt % of coke relative to the total catalyst weight, and then dividing by the weight fraction of molecular sieve. In a preferred embodiment, the weight fraction of molecular sieve within the SAPO catalyst is 0.6 wt %.

In various embodiments, operating at an increased level of coke on regenerated catalyst can lead to reduced degradation of catalyst, in part due to a lower catalyst residence time in the regenerator for burning a desired coke load. However, operating at increased levels of coke on regenerated catalyst requires selection of targeted regeneration conditions so that the increased coke level is maintained without causing excessive afterburn or other undesired side effects. Additionally, the targeted regeneration conditions should maintain the desired coke level during steady state operation of the reaction system, i.e., the average coke level on catalyst in the reactor should stay at a desired level, and the amount of coke remaining on catalyst particles exiting the regenerator should remain at a desired level.

We have found that for regeneration temperatures below conventional regeneration temperatures of typically 600° C. to 700° C., such as described herein, the performance of the molecular sieve catalyst may be improved. This may be explained by the fact that a hydrocarbon pool is maintained in the sieve as this does not need to be rebuilt every time following regeneration. Also, it is possible that during regeneration at lower temperatures, the outer layer of hydrocarbon deposits are removed and the innermost acid sites are retained which can improve the activity of the catalyst following regeneration.

In a preferred embodiment, the catalyst may be regenerated following pretreatment under a controlled set of conditions in order to reduce or eliminate damage or degradation of the catalyst. In order to achieve the reduced degradation, the following conditions are simultaneously implemented in the regenerator: a regeneration temperature of from 500° C. to 650° C., preferably at least 590° C.; 0.5% to 2.5% oxygen by volume in the flue gas exiting the regenerator; a catalyst residence time or hold-up time in the regenerator of less than 30 minutes, more preferably at least 5 minutes, and still more preferably from 20 to 25 minutes; a coke level on the regenerated catalyst of at least 0.6 wt % relative to the weight of molecular sieve; a regenerator pressure of from 137 to 206 kPag (20 to 30 psig).

In one embodiment, the rate at which the catalyst is recirculated to recontact the feed within the reactor, is from 1 to 100 times, more desirably from 10 to 80 times, and most desirably from 10 to 50 times the total feed rate, by weight, of oxygenates to the reactor.

In another embodiment, a portion of the catalyst, comprising molecular sieve and any other materials (such as matrix materials, binders, fillers, etc.) can be removed from the reactor for regeneration and for recirculation/reintroduction back to the reactor at a rate (catalyst weight/hour) from 0.01 times to 5 times, more desirably from 0.025 times to 2 times or from 0.1 times to 0.5 times, and most desirably from 0.1 to 0.3 times the total feed rate (oxygenate weight/hour) of oxygenates to the reactor system. These rates pertain to the formulated molecular sieve catalyst composition, including non-reactive solids and they may encompass pretreatment of all of the catalyst prior to regeneration or pretreatment of all of the catalyst before regeneration.

The oxidizing medium may comprise at least a stoichiometric amount of oxygen for completely removing coke from the catalyst. Preferably, the oxidizing medium comprise an amount of oxygen to ensure complete removal of coke from the sieve catalyst. Typically the amount of oxygen is between 5% to 200% relative to stoichiometric amount of oxygen, preferably between 105% to 120% relative to the stoichiometric amount of oxygen. In a preferred embodiment, oxygen is present in an amount of 5 to 20% more than the stoichiometric amount which results in 0.5 to 3% by volume in the flue gas leaving the regenerator.

Preferably, the amount of oxygen in the regeneration flue gas (i.e., gas which leaves the regenerator) is at least 0.5% by volume, or at least 1.5% by volume, or at least 2.0%, or at least 2.2%, or at least 2.5%. In another embodiment, the amount of oxygen in the regeneration flue gas is not greater than 6.0% by volume, or not greater than 4.0% by volume, or not greater than 3.0% by volume.

Non-limiting examples of suitable regeneration oxidizing media include one or more of oxygen, $O_3$, $SO_3$, $N_2O$, $NO$, $NO_2$, $N_2O_5$, air, air diluted with nitrogen or carbon dioxide, oxygen and water (U.S. Pat. No. 6,245,703), carbon monoxide and/or hydrogen.

In an embodiment, the temperature within the regeneration apparatus can be controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration apparatus and passing it through a catalyst cooler to form a cooled regenerated catalyst composition. The catalyst cooler, in an embodiment, is a heat exchanger that is located either internal or external to the regeneration system. Other methods for operating a regeneration system are disclosed in U.S. Pat. No. 6,290,916 (controlling moisture).

The regenerated catalyst composition withdrawn from the regeneration apparatus, preferably from the catalyst cooler, is combined with a fresh molecular sieve catalyst composition and/or re-circulated molecular sieve catalyst composition and/or feedstock and/or fresh gas or liquids, and returned to the reactor(s). In one embodiment, the regenerated catalyst composition withdrawn from the regeneration apparatus is returned to the reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor, preferably to the one or more reactor(s). There are many techniques for controlling the flow of a catalyst composition as described by Michael Louge in *Experimental Techniques, Circulating Fluidized Beds* 336-337 (Grace, Avidan and Knowlton, eds., Blackie, 1997).

Finally, in a further embodiment, there is provided a method of regenerating a molecular sieve catalyst for converting oxygenates into olefins, comprising in a single regeneration stage in the absence of pretreatment, regenerating the catalyst under regeneration conditions by heating the catalyst at a regeneration temperature of between 300° C. to 480° C., preferably 450° C., in an oxidizing medium for a regeneration residence time of between 1 to 30 minutes, preferably 10 minutes.

Even for single stage regeneration, in the absence of a catalyst pretreatment stage, we have found that for regeneration temperatures below conventional regeneration temperatures of typically 600° C. to 700° C. the performance of the molecular sieve catalyst may be improved. This may be explained by the fact that a hydrocarbon pool is maintained in the sieve as this does not need to be rebuilt every time following regeneration.

Molecular Sieve Material

The molecular sieves useful in the process described herein are preferably silicoaluminophosphate (SAPO) molecular sieves, aluminophosphate (AlPO) molecular sieves, metal substituted versions thereof, and/or combinations thereof.

In one embodiment, the silicoaluminophosphate molecular sieve is represented, on an anhydrous basis, by the formula:

$$mR:(Si_xAl_yP_z)O_2$$

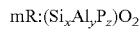

wherein R represents at least one templating agent, preferably an organic templating agent; m is the number of moles of R per mole of $(Si_xAl_yP_z)O_2$ and m has a value from 0 to 1, preferably 0 to 0.5, and most preferably from 0 to 0.3; x, y, and z represent the mole fraction of Al, P and Si as tetrahedral oxides. In an embodiment, m is greater than or equal to 0.2, and x, y and z are greater than or equal to 0.01. In another embodiment, m is greater than 0.1 to 1, x is greater than 0 to 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

In one embodiment, the silicoaluminophosphate molecular sieves have an Si/Al ratio of not greater than 0.5, preferably not greater than 0.3, more preferably not greater than 0.2. In another embodiment, the Si/Al ratio is sufficiently high to allow for increased catalytic activity of the molecular sieve. Preferably, the silicoaluminophosphate molecular sieves contain Si and Al at a ratio of at least 0.005, more preferably at least 0.01, and most preferably at least 0.02.

Non-limiting examples of SAPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and metal containing molecular sieves thereof. Particularly useful molecular sieves include, but are not limited to, one or a combination of SAPO-18, SAPO-34, SAPO-35, SAPO-44, SAPO-56, AlPO-18, AlPO-34, and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

In an embodiment, the molecular sieve is an intergrowth material having two or more distinct crystalline phases within one molecular sieve composition, such as a molecular sieve composition containing SAPO-18, which has an AEI framework-type, and SAPO-34, which has a CHA framework-type. Thus, the molecular sieve used herein may comprise at least one intergrowth phase of AEI and CHA framework-types, especially where the ratio of CHA framework-type to AEI framework-type, as determined by the DIFFaX method disclosed in US 2002-0165089, is greater than 1:1.

Oxygenate to Olefin Reaction Systems

The conversion of oxygenates to produce light olefins may be carried out in a variety of large scale catalytic reactors, including, but not limited to, fluid bed reactors and concurrent riser reactors as described in *Fluidization Engineering* (D. Kunii and O. Levenspiel, Robert E. Krieger Publishing Co. NY, 1977). Additionally, countercurrent free fall reactors may be used in the conversion process. See, for example, U.S. Pat. No. 4,068,136 and *Fluidization and Fluid-Particle Systems* 48-59 (F. A. Zenz and D. F. Othmer, Reinhold Publishing Corp., NY 1960).

In one embodiment, the gas and solid particles are flowed through the gas-solids reactor system at a weight hourly space velocity (WHSV) of from 1 $hr^{-1}$ to 5,000 $hr^{-1}$, preferably from 5 $hr^{-1}$ to 3,000 $hr^{-1}$, more preferably from 10 $hr^{-1}$ to 1,500 $hr^{-1}$, and most preferably from 20 $hr^{-1}$ to 1,000 $hr^{-1}$. In one preferred embodiment, the WHSV is greater than 25 $hr^{-1}$, and up to 500 $hr^{-1}$. WHSV is defined as the total weight per hour of the gas flowing between reactor walls divided by the total weight of the solids flowing between the same segment of reactor walls. The WHSV is maintained at a level sufficient to keep the catalyst composition in a fluidized state within a reactor.

Another embodiment directed toward use of cyclones in conjunction with a riser reactor, the gas and solid particles are flowed through the gas-solids reactor system at a gas superficial velocity (GSV) at least 1 meter per second (m/sec), preferably greater than 2 m/sec, more preferably greater than 3 m/sec, and most preferably greater than 4 m/sec. The GSV should be sufficient to maintaining the solids in a fluidized state, particularly in a fast fluidized state.

In yet another embodiment, the solids particles and gas are flowed through the gas-solids reactor at a solids loading of at least 0.1 $lb/ft^3$ (1.6 $kg/m^3$), or at least 0.5 $lb/ft^3$ (8 $kg/m^3$), or at least 1.0 $lb/ft^3$ (16 $kg/m^3$), or at least 2.0 $lb/ft^3$ (32 $kg/m^3$), or at least 4.0 $lb/ft^3$ (64 $kg/m^3$). Alternatively, the solids loading can be 5 $lb/ft^3$ (80 $kg/m^3$) or less, or 4.0 $lb/ft^3$ (64 $kg/m^3$) or less, or 2.0 $lb/ft^3$ (32 $kg/m^3$) or less.

In one practical embodiment, the process is conducted as a fluidized bed process or high velocity fluidized bed process utilizing a reactor system, a regeneration apparatus and a recovery system. In such a process the reactor system conveniently includes a fluid bed reactor system having a first reaction region consisting of various fast fluid or dense fluid beds in series or parallel and a second reaction region within at least one disengaging vessel, comprising two or more cyclones configured and/or operated according to various embodiments. In one embodiment, the fast fluid or dense fluid beds and disengaging vessel are contained within a single reactor vessel. Fresh feedstock, preferably containing one or more oxygenates, optionally with one or more diluent(s), is fed to the one or more fast fluid or dense fluid beds reactor(s) into which a molecular sieve catalyst composition or coked version thereof is introduced. In one embodiment, prior to being introduced to the reactor(s), the molecular sieve catalyst composition or coked version thereof is contacted with a liquid and/or vapor, preferably water and methanol, and a gas, for example, an inert gas such as nitrogen.

In an embodiment, the amount of fresh feedstock fed as a liquid and/or a vapor to the reactor system is in the range of from 0.1 wt % to 99.9 wt %, such as from 1 wt % to 99 wt %, more typically from 5 wt % to 95 wt % based on the total weight of the feedstock including any diluent contained therein. The liquid and vapor feedstocks may be the same composition, or may contain varying proportions of the same or different feedstocks with the same or different diluents.

The OTO process described herein can be conducted over a wide range of temperatures, such as in the range of from 200° C. to 1000° C., for example from 250° C. to 800° C., including from 250° C. to 750° C., conveniently from 300° C. to 650° C., typically from 350° C. to 600° C., and for example from 350° C. to 550° C.

Similarly, the OTO process described herein can be conducted over a wide range of pressures including autogenous pressure. For instance, light olefins will form, though not necessarily in optimal amounts, at a wide range of pressures including, but not limited to, pressures from 0.1 kPaa to 5 MPaa, such as from 5 kPaa to 1 MPaa, and conveniently from 20 kPaa to 500 kPaa. The foregoing pressures do not include that of a diluent, if any, and refer to the partial pressure of the feed as it relates to oxygenate compounds and/or mixtures thereof. Pressures outside of the stated ranges may be used and are not excluded from the process described herein. Lower and upper extremes of pressure may adversely affect selectivity, conversion, coking rate, and/or reaction rate; however, light olefins will still form and, for that reason, the process may be carried out at these extremes of pressure.

In certain embodiments, the average coke level on catalyst in the reactor is at least 2.25% by weight relative to the total weight of catalyst, or at least 3% by weight, or at least 5% by weight, or at least 6% by weight. In preferred embodiments, the coke content of the catalyst at the point where the (oxygenate) feedstock contacts/mixes with the regenerated catalyst is at least 0.5 wt %, as measured on the molecular sieve, and/or at least 1 wt %, as measured on the catalyst composition (e.g., including binder, matrix, etc.). In other preferred embodiments, the coke content of the catalyst at the point where the (oxygenate) feedstock contacts/mixes with the regenerated catalyst may additionally or alternately be no greater than 2 wt %, for example no greater than 1.2 wt %, as measured on the molecular sieve, and/or no greater than 4 wt %, for example no greater than 2.4 wt %, as measured on the catalyst composition (e.g., including binder, matrix, etc.).

Olefin Usage

The olefin products, especially the light olefins comprising ethylene and propylene, are useful in polymerization processes that include solution, gas phase, slurry phase and high pressure processes, or a combination thereof. Particularly preferred is a gas phase or a slurry phase polymerization of one or more olefins) at least one of which is ethylene or propylene. These polymerization processes utilize a polymerization catalyst that can include any one or a combination of the molecular sieve catalysts discussed above, however, the preferred polymerization catalysts are Ziegler-Natta, Phillips-type, metallocene, metallocene-type and advanced polymerization catalysts, and mixtures thereof. The polymers produced by the polymerization processes described above; include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

In an embodiment, the integrated process comprises a polymerizing process of one or more olefins) in the presence of a polymerization catalyst in a polymerization reactor to produce one or more polymer products, wherein one or more olefins) are made by the before described oxygenate to olefins process, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator. Preferably the activator is a non-coordinating anion or alumoxane, or combination thereof, and most preferably the activator is alumoxane.

In addition to polyolefins, numerous other olefin derived products are formed from the olefin(s) recovered by any one of the processes described above, particularly the conversion processes, more particularly the GTO process or MTO process. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

Figure 1B:
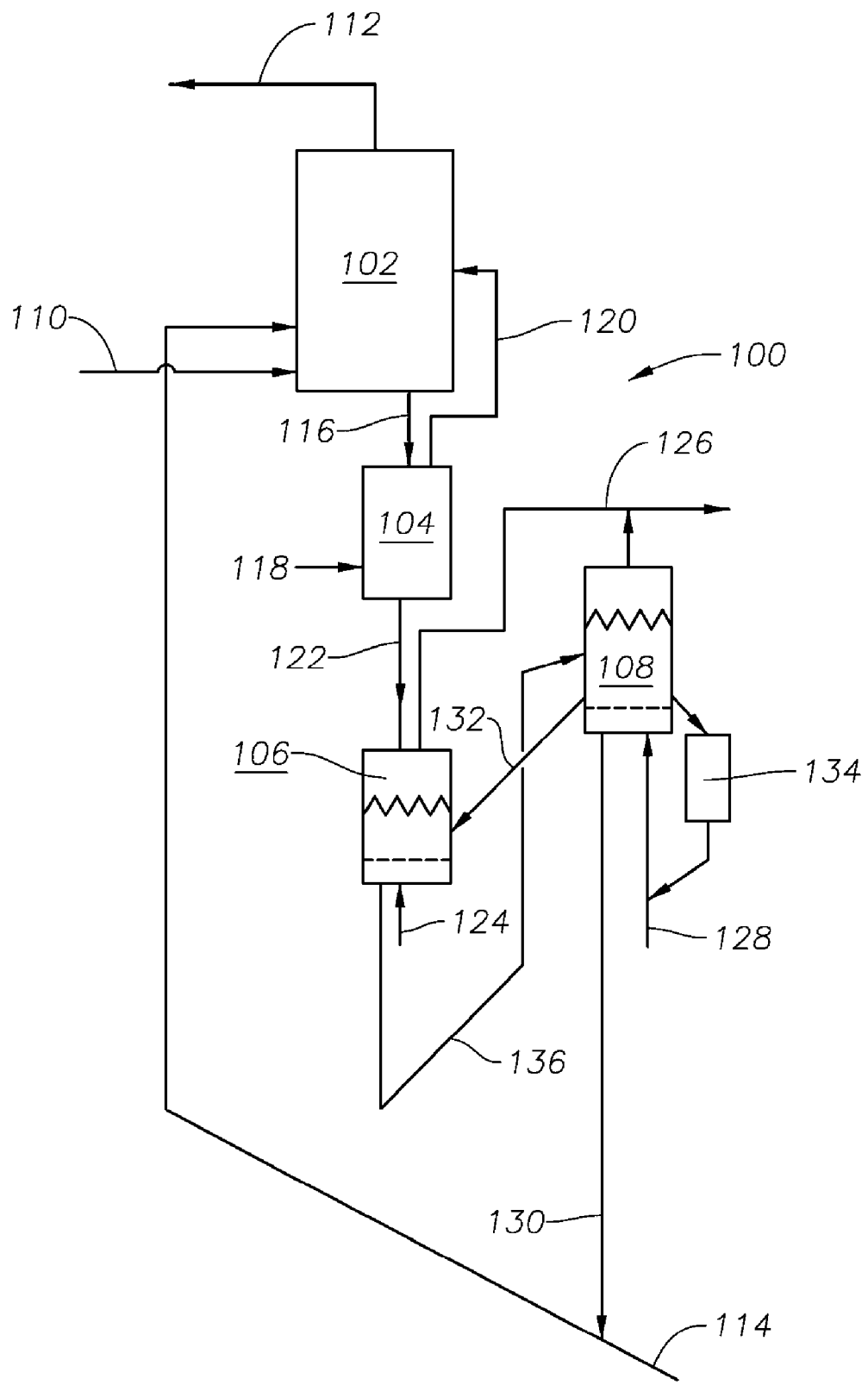
FIG. 1b shows a diagrammatic layout of an OTO conversion process according to another embodiment.
Figure 1C:
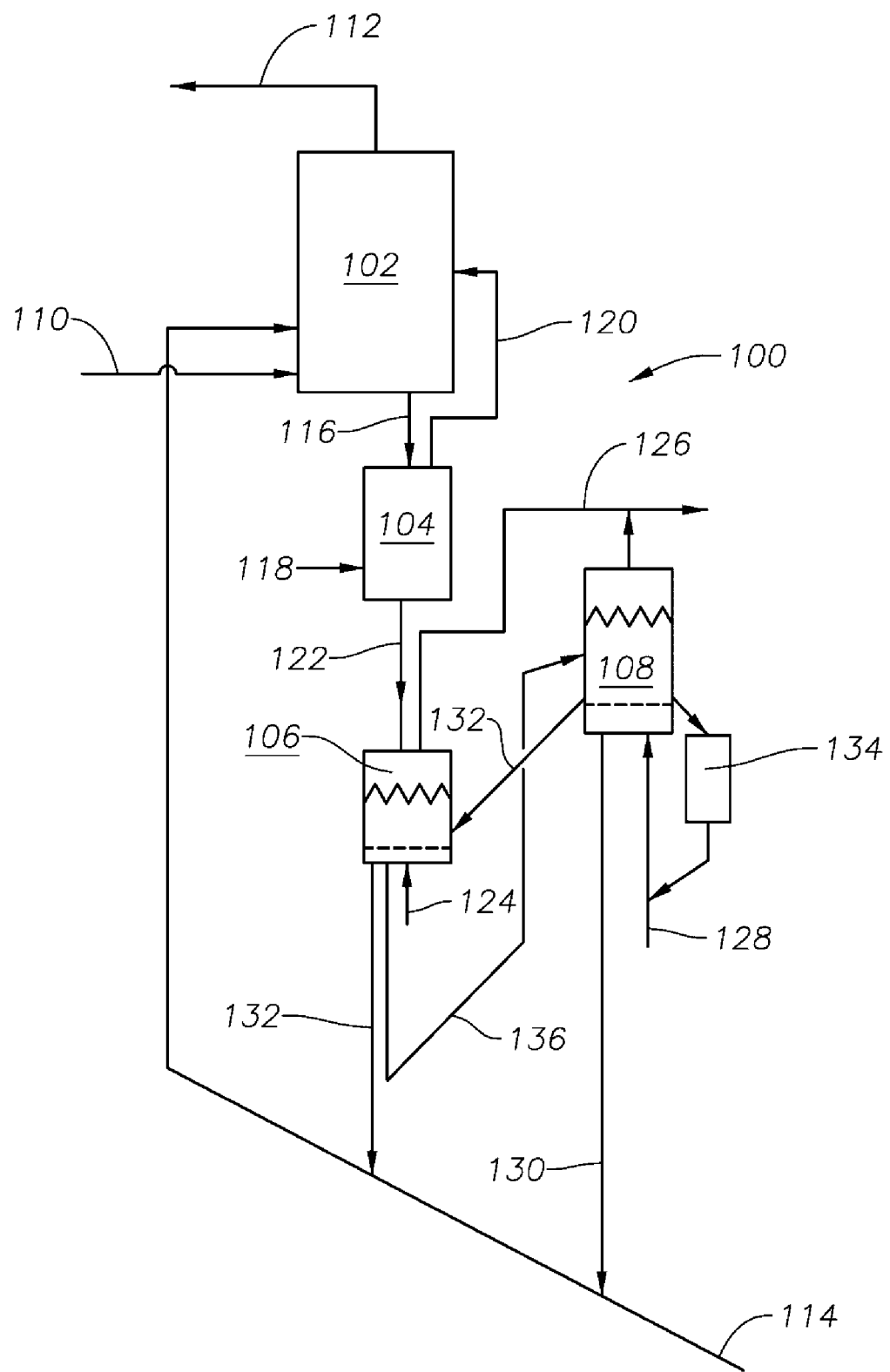
FIG. 1c shows a diagrammatic layout of an OTO conversion process according to a further embodiment.

FIGS. 1a, 1b and 1c present three process lay-out embodiments for OTO units in which the regeneration apparatus has been implemented. In all Figures, the lay-outs comprise a two stage process. Corresponding components have been given the same reference numeral.

The OTO unit 100 of FIG. 1a comprises a reactor 102 in which the oxygenate conversion takes place, a separator or stripper 104 for stripping catalyst from the oxygenate product, a pretreater 106 for pretreating the catalyst, a regenerator 108 for regenerating the catalyst, and a catalyst cooler 134.

Feed enters the reactor 102 via line 110 and vapor and reactor effluent leave the reactor at the top via line 112. Spent catalyst is transferred to the stripper 104 via line 116. The reactor 102 operates in a fluidized bed mode with the catalyst being fluidized by the vaporized feeds and products.

The catalyst is stripped by means of a flow of steam 118. Stripping vapors are fed back to the reactor 102 via line 120. The stripped catalyst is transferred from the stripper via line 122 to the pretreater 106. In the pretreater 106, the coke on the catalyst is partially combusted in an oxygen depleted medium by means of the feed of inert gas and oxygen via line 124.

Exhaust gases from the pretreater 106 are combined with the flue gas from the regenerator 108 via line 126. The pretreated catalyst from the pretreater 106 is transferred via line 136 to the regenerator 108.

In the regenerator 108 the catalyst is regenerated by means of the air stream 128 which combusts the coke deposits on the catalyst. The regenerated catalyst is transported via line 130 back to the reactor 102. The catalyst cooler 134 helps to maintain the regenerator at the desired temperature. The lift stream via line 114 transports regenerated catalyst to the reactor.

In a particular embodiment, the coked spent catalyst from the reactor 102 is first heated up from the reactor temperature of 450 to 500° C. up to the pretreatment temperature of 650° C. in an oxygen depleted atmosphere. The spent catalyst is held at 650° C. for up to as much as 20 minutes, and is then directed to the regenerator 108. In the pretreatment stage there may no excess oxygen and the catalyst may heated at a treatment temperature of, for example, 650° C. In the final step the pretreated catalyst enters a regeneration vessel where it is exposed to excess oxygen at levels from 0.5 to 5% in the flue gas 128 and the majority of the coke on the catalyst is burned off typically yielding a regenerated catalyst containing 0.05 to 0.5 wt % coke on catalyst. The final regenerated catalyst is then directed to the reactor 102.

In a particular embodiment, in the process of FIG. 1a the spent coked catalyst is heated in the catalyst treater for 20 minutes in a low oxygen environment at, for example 650° C. The temperature of 650° C. may be achieved by a combination of a preheated pretreatment medium and a minimal amount of combustion of coke on the spent catalyst by limiting the oxygen injected to an amount of 20% or less of the stoichiometric amount required to burn all the coke at that catalyst circulation rate.

The process as shown in FIG. 1b is very similar to the process of FIG. 1a. In FIG. 1b the spent coked catalyst is heated in the catalyst heater by mixing it with hot regenerated catalyst from the regenerator which is fed to the pretreater 106 via line 132. The pretreatment medium in this process is an inert gas in the form of nitrogen which is fed to the pretreater via line 123. Therefore the pretreatment environment is completely devoid of oxygen. Otherwise the layout of the process and its operations including the operating conditions, are identical to the process of FIG. 1a.

The process as shown in FIG. 1c is very similar to the process of FIG. 1b. In FIG. 1c a portion of the catalyst from the pretreater is returned to the reactor via line 132. In this way, catalyst containing hydrocarbon co-catalyst which is retained within the pore structure is returned to the reactor. Otherwise, the layout of this process and its operations including the operating conditions, are identical to the process of FIGS. 1a and 1b.

The processes of FIGS. 1a, 1b and 1c may further include an additional line (not shown) which feeds gaseous effluent from the pretreater 106 to the regenerator 108. As the pretreater operates at less than stoichiometric oxygen levels, significant amounts of carbon monoxide are produced. The regenerator 108 combusts any carbon monoxide in the effluent gas from the pretreater to control the carbon monoxide.

EXAMPLES

In conventional OTO catalyst regeneration a single stage fluidized bed regenerator is used to at least partially remove the coke deposited on the spent catalyst. The average coke level from the OTO reactor is 6 grams carbonaceous deposits per 100 grams of catalyst, and the coke after regeneration is 0.3-0.5 grams carbonaceous deposits per gram of catalyst. In addition, conventional OTO regenerators are designed to operate in an excess air environment to prevent the reaction of coke with the lattice oxygen of SAPO materials, known as redox behavior. In the following Examples, we will compare conventional regeneration with the regeneration process described herein.

Experimental Techniques

Coke Measurement—The coke on the MTO spent catalyst was characterized in temperature programmed oxidation (TPO) units. A diluted oxygen gas mixture (typically 1-11% $O_2$ in helium or $N_2$) was used to burn the coke while the temperature was increased in steps. The combustion effluent was sent to a catalytic converter which contained platinum catalyst to convert CO to $CO_2$. In a regeneration unit, a non-dispersive infrared (NDIR) detector was equipped to measure the concentration of $CO_2$ which provided the $CO_2$ concentration response curve to the temperature. The amount of coke on the catalyst which had been removed was then quantified by comparing the integrated area of this TPO curve with that of a calibration standard. In another regeneration unit, the combustion effluent passed through a nickel containing methanator, which converted CO and $CO_2$ into methane in the presence of an excess amount of hydrogen. The concentration of methane was then quantified by an FID (flame ionization detector). Similarly, the amount of coke on the catalyst was then measured by comparing the integrated area of the FID TPO curve with that of a calibration standard. The techniques are for example outlined in, 71(3) J. THERMAL ANALYSIS & CALORIMETRY 867-874 (2003).

Gas Chromatography (GC) Analysis—the collected effluent samples were analyzed by on-line gas chromatography (Hewlett Packard 6890) equipped with a flame ionization detector. The chromatographic column used was a Porapak Q column. The response factors used are listed in the below Table 1, wherein "C°" refers to the saturated hydrocarbon and "C=" refers to the unsaturated double bond-containing hydrocarbon.

TABLE 1

| | Response factors. | | | | | | | | | |
|---|---|---|---|---|---|---|---|---|---|---|
| | $C_1$ | $C_2$= | $C_2°$ | $C_3$= | $C_3°$ | $CH_3OH$ | $(CH_3)_2O$ | $C_5$ | $C_6$ | $C_7$ |
| Response factor | 1.103 | 1.000 | 1.070 | 1.003 | 1.052 | 3.035 | 2.639 | 0.999 | 1.006 | 1.000 |

Comparative Example 1

A catalyst sample was prepared from 50 mg of a formulated SAPO-34 catalyst with 45 wt % sieve content mixed uniformly with SiC particles (60-100 mesh) in a weight ratio of 1:4 to mitigate the heat excursion during the exothermic methanol to olefins (MTO) reactions and the regeneration coke burn reactions. The mixture was loaded into a tubular microflow reactor. The reactor was made from ¼" siliconsteel tubing. The catalyst was exposed to the following MTO testing conditions for 20 minutes in a fixed bed reactor: pressure 172 kPag (25 psig), temperature of 500° C., WHSV=100 grams MeOH/grams sieve/hr. To regenerate the coked catalyst, the catalyst bed temperature was held for 3 min at 300° C. under a flow of $N_2$ to remove methanol and other light reaction intermediates. Under a flow of 11 volume % $O_2$ in $N_2$, the catalyst bed temperature was subsequently increased in steps (ramps) to 650° C. with a 15° C./min ramping rate, and held at 650° C. for 20 minutes.

Figure 2:
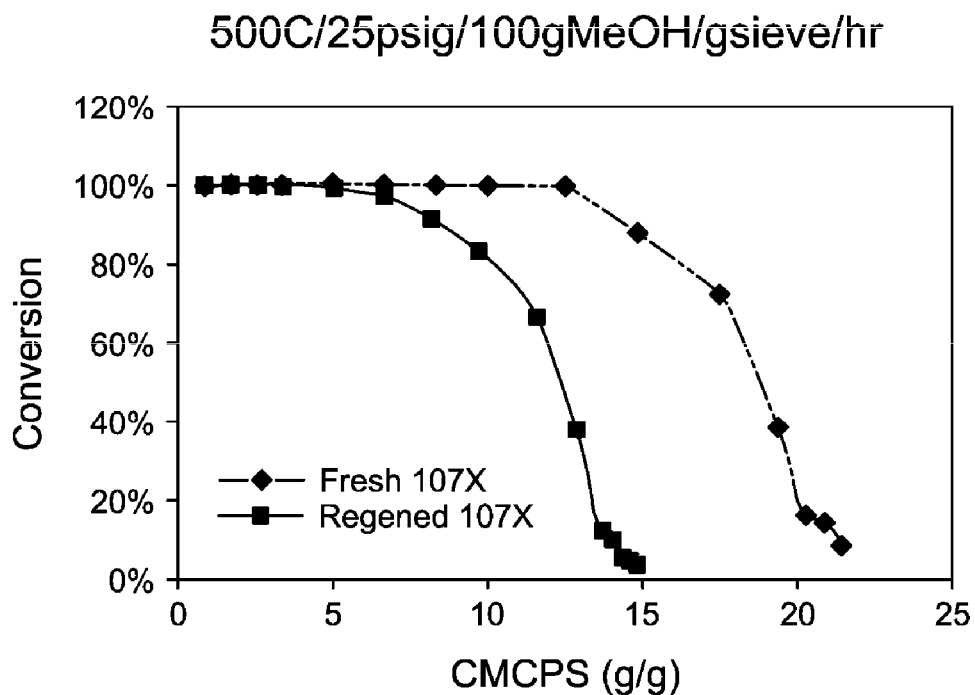
FIG. 2 shows conversion as a function of cumulated methanol converted per sieve weight for fresh and regenerated catalyst prepared in accordance with Comparative Example 1.
Figure 3:
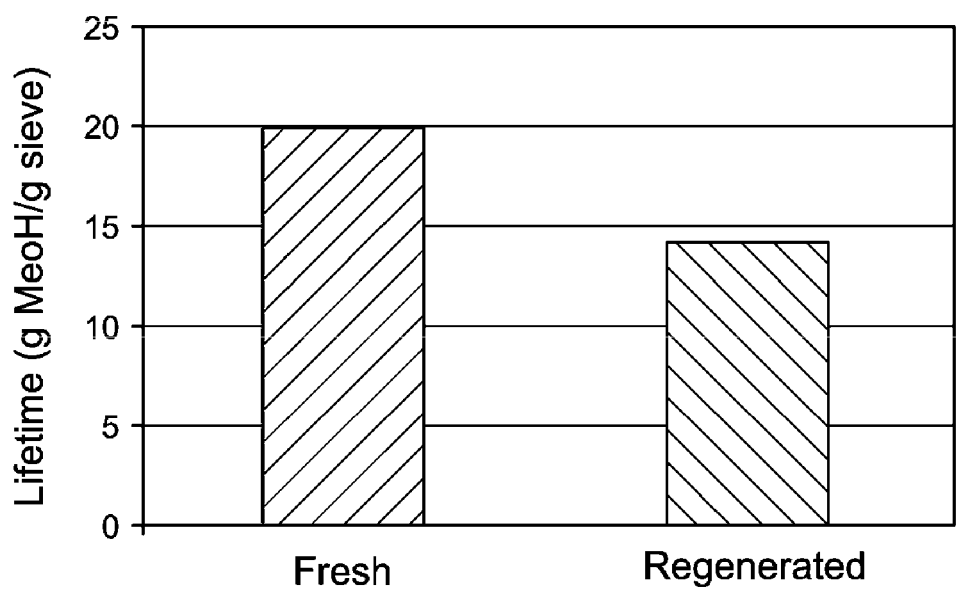
FIG. 3 shows life time of fresh and regenerated catalyst prepared in accordance with Comparative Example 1.

FIG. 2 shows the catalyst deactivation curves for both fresh and regenerated catalysts during a fresh-to-death run. It is observed that the regenerated catalyst deactivates much faster than the fresh catalyst. The catalyst life as shown in FIG. 3, defined as cumulated methanol converted per sieve weight (CMCPS) above 10% conversion, has been significantly shortened after regeneration.

Figure 4:
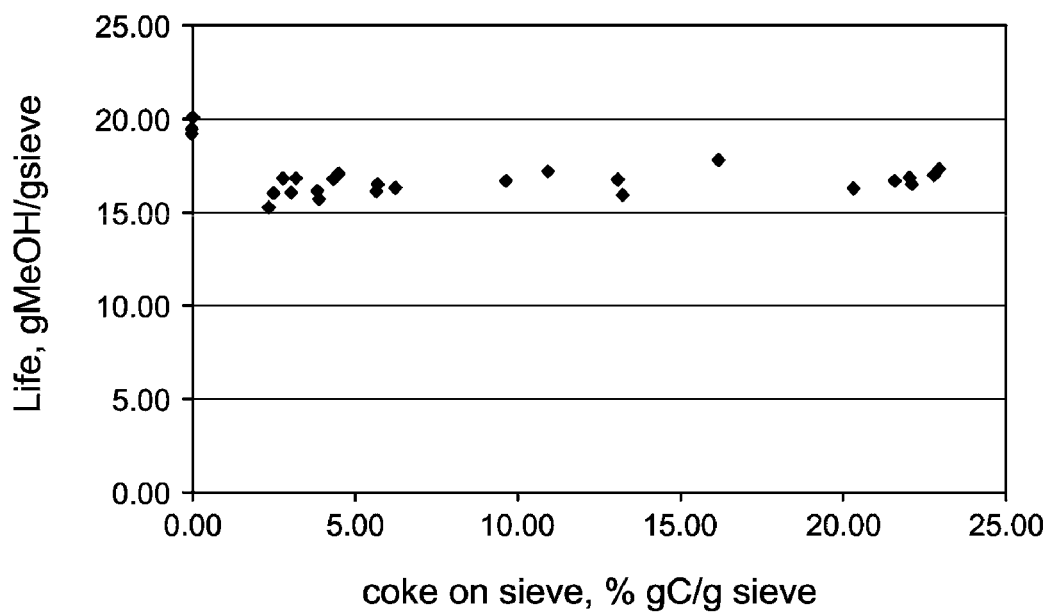
FIG. 4 shows the catalyst life was a function of coke on sieve for regenerated catalyst in accordance with Comparative Example 1.

FIG. 4 shows the lifetime for a second cycle catalyst (i.e., after a full regeneration) on the Y axis and the coke on catalyst at the end of the first cycle of MTO (that is the coke on catalyst at the end of a run that started with fresh catalyst). It can be seen that even a small amount of coke deposited on fresh catalyst can lead to shorter lifetimes in subsequent cycles after the catalyst has been regenerated.

Example 2

The catalyst used in this Example was again a formulated SAPO-34 sieve catalyst with 45 wt % sieve content. A catalyst sample was prepared from 50 mg of this SAPO catalyst, mixed uniformly with SiC particles (60-100 mesh particle size corresponding to a particle diameter of 180 to 250 microns) with a weight ratio of 1:4 to mitigate the heat released during the exothermic MTO reactions and the regeneration coke burn reactions. The mixture was loaded into a tubular microflow reactor which was identical to the reactor used in Comparative Example 1. The catalyst was exposed to the following MTO testing conditions: pressure 172 kPag (25 psig), temperature of 500° C., WHSV=100 grams MeOH/ grams sieve/hr.

The deactivated catalyst was regenerated as follows in a regeneration unit in two stages comprising a pretreatment stage and a regeneration stage. First, under an inert gas flow of nitrogen (25 sccm), the catalyst bed was heated up to a first temperature of 300° C. and held at this temperature for 3 minutes. The bed temperature was then ramped to a second temperature of 650° C. with a 15° C./minute ramping rate and held at 650° C. for 20 minutes before cooling down to room temperature. Subsequently, the catalyst was regenerated with 11% oxygen in nitrogen with the same temperature profile as above. After the catalyst pretreatment and regeneration, the reactor tubes were taken back to the MTO reaction unit to evaluate performance.

Figure 5:
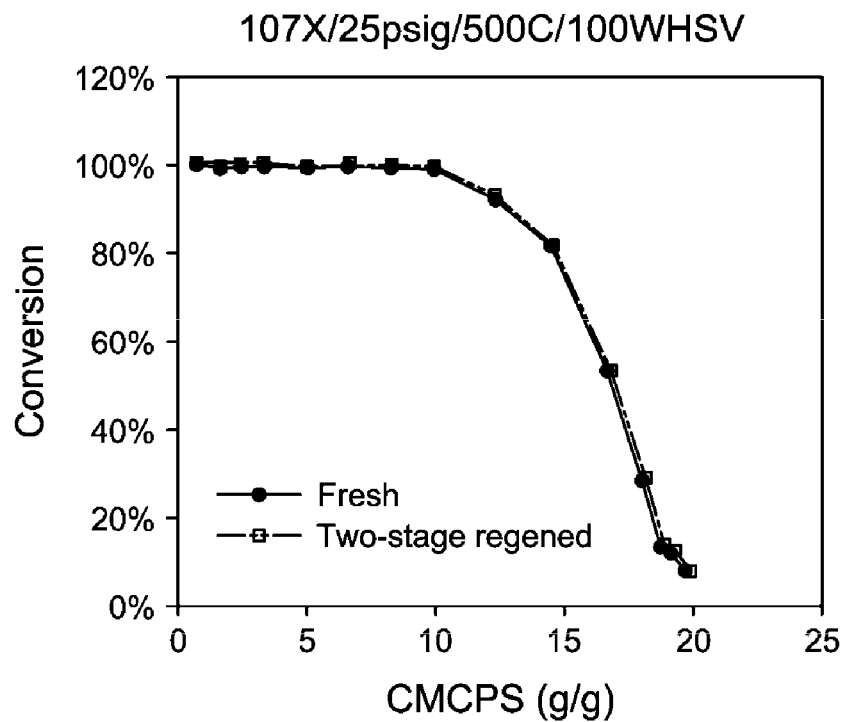
FIG. 5 shows conversion as a function of cumulated methanol converted per sieve weight for fresh and regenerated catalyst prepared in accordance with Example 2.
Figure 6:
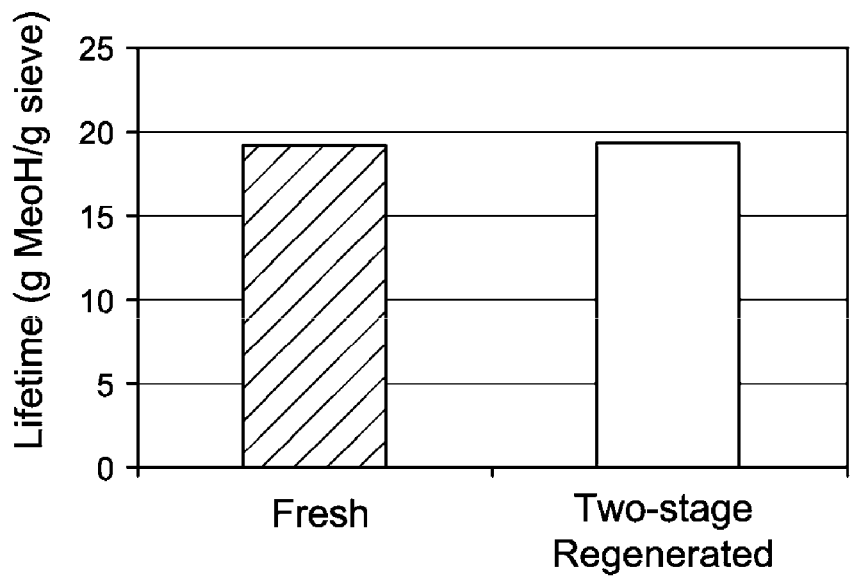
FIG. 6 shows life time of fresh and regenerated catalyst prepared in accordance with Example 2.

FIG. 5 shows the comparison of activity profile between the fresh catalyst and the two-stage treated and regenerated catalyst. It can be seen that the performance of the regenerated catalyst is identical to the fresh catalyst. The lifetime of the catalyst was fully recovered as shown in FIG. 6. The prime olefins selectivity and other critical performance parameters remain unchanged after the two-stage regeneration process, as shown in Table 2 below.

TABLE 2

Reaction products and prime olefin selectivity (POS).

| Example | Feed | $T_{reactor}$ (° C.) | WHSV (hr$^{-1}$) | C1 (wt %) | C2= (wt %) | C2° (wt %) | C3= (wt %) | C3o (wt %) | C4= (wt %) | C5+ (wt %) | Coke (wt %) | POS (wt %) |
|---|---|---|---|---|---|---|---|---|---|---|---|---|
| 1 | MeOH | 500 | 100 | 2.91 | 42.01 | 0.47 | 35.61 | 0.72 | 10.45 | 2.98 | 4.18 | 77.62 |
| 2 | MeOH | 500 | 100 | 3.00 | 41.91 | 0.47 | 35.42 | 0.75 | 10.45 | 3.06 | 4.25 | 77.33 |

In the pretreatment stage "soft coke" known as single alkylated light aromatics and adsorbed methanol are removed from the catalyst. In the regeneration stage, subsequent rich oxygen burn gave a typical temperature programmed oxidation profile and the remaining coke deposit was burned off.

Compared to the one-step full burn as disclosed in Comparative Example 1, the two-stage, high temperature treatment in a relatively inert atmosphere followed by regeneration in an oxidized medium greatly improves recovery of catalyst activity and improves the process efficiency.

Example 3

A catalyst sample was prepared from 95 mg of a formulated SAPO catalyst mixed with 1 grams of SiC. The mixture was again loaded into a tubular microflow reactor. The reactor was made from ¼" silicon steel tubing. The reactor temperature was increased to 475° C. while the catalyst was under Helium flow (24 ml/minute) for 30 to 40 minutes until the temperature stabilized. Methanol was flowed through the reactor at 80 microliter/minute at 475° C., 172 kPag (25 psig) and 100 WHSV. The reactor effluent was sampled in a multi-loop sampling valve to obtain the gas selectivity data.

The experiment was started by fully coking up a catalyst in a microflow reactor by running enough methanol through the catalyst so that the methanol conversion reached 10 wt % or less at 475° C., 25 psig and 100 WHSV. The coked catalyst sample was regenerated at 475° C. and at ambient pressure without pretreatment. A mixture of 10 ml/minute of oxygen and 10 ml/minute of He was flowed through the reactor for catalyst regeneration to ensure that the supply of oxygen was not the rate limiting step in burning the coke (full burn), therefore ensuring a more or less homogeneous coke removal along the catalyst bed. Immediately after the 50:50 $O_2$/He mixture exited the reactor, a He stream at 30 ml/minute was combined with regenerator effluent to dilute the oxygen concentration in the gas stream, primarily for safety concerns.

The regenerated catalyst was then tested for MTO performance at 475° C. and 25 psig by feeding MeOH at 100 WHSV until the total amount of MeOH fed was equivalent to 7 grams of MeOH per gram of sieve. The sample resulting from the MTO performance test was then regenerated using the same conditions described for the first regeneration cycle and the MTO performance was measured again. This was repeated to obtain MTO performance data after each of a total of 47 regeneration cycles.

Typically five gaseous samples were analyzed to obtain the weight average selectivities shown in Table 3. The weight average selectivities were calculated based on the following formula, $x_1*y_1+(x_2-x_1)*(y_1+y_2)/2+(x_3-x_2)*(y_2+y_3)/2+\ldots$, where xi and yi are yield, and grams methanol fed/grams sieve, respectively. The reported lifetime of catalysts (in g/grams catalyst) in the Table is methanol that was cumulatively converted. Both the lifetime and WHSV in the Table are based on the weight of the sieve.

The typical conversion at the end of the 7 g/grams sieve methanol flow was ca. 40 wt %. After the 7 grams/grams sieve of methanol flow (7 g/g sieve), the catalyst was mildly regenerated at 475° C. for 10 min to repeat the cycle.

Figure 7:
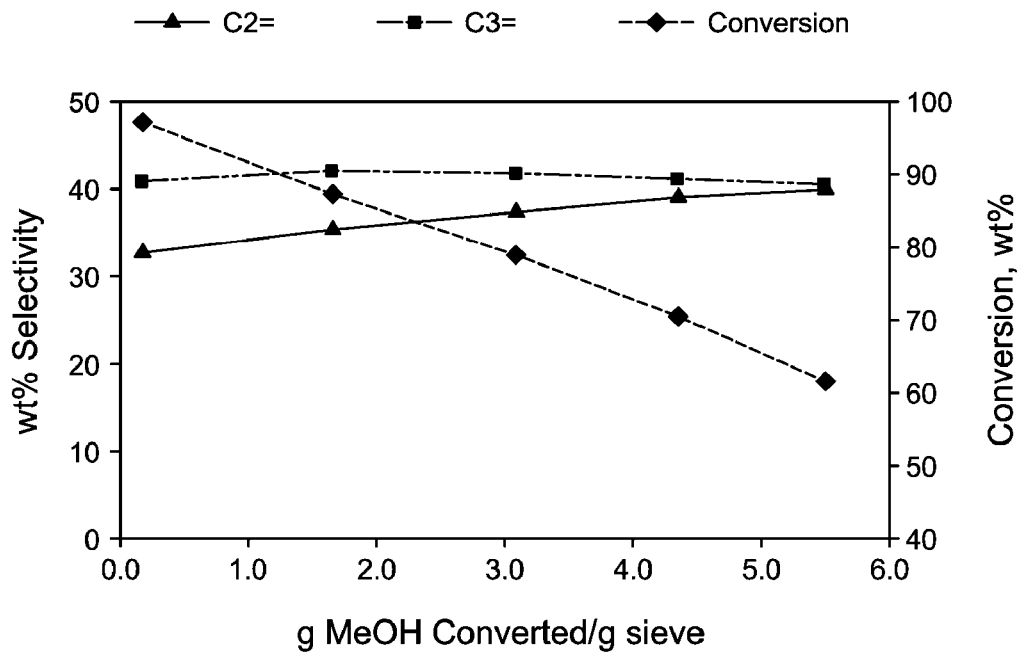
FIG. 7 shows the conversion and prime olefins selectivity as a function of cumulatively converted grams (g) methanol per gram of sieve in accordance with Example 3.

FIG. 7 shows a representative plot of conversion and prime olefins selectivity vs. cumulatively converted grams methanol/grams sieve for one of the mildly-regenerated samples. Propene selectivity remained nearly flat throughout the run.

Table 3 summarizes the MTO performance selectivities of a catalyst that was mildly regenerated for 47 times. The average MTO performance selectivity for samples resulting from the 47 mild regenerations is also shown in Table 3.

TABLE 3

Weight average selectivity MTO performance data for a mildly-regenerated catalyst at 475° C., 25 psig and 100 WHSV.

| # of Regen | C1 (wt %) | C2= (wt %) | C2° (wt %) | C3= (wt %) | C3° (wt %) | C4= (wt %) | C5+ (wt %) | Coke (wt %) | POS (wt %) | Lifetime (g/g) |
|---|---|---|---|---|---|---|---|---|---|---|
| 1 | 1.67 | 35.72 | 0.24 | 40.18 | 0.41 | 13.07 | 5.07 | 3.65 | 75.90 | 4.58 |
| 2 | 1.69 | 36.24 | 0.25 | 40.38 | 0.44 | 13.16 | 5.01 | 2.83 | 76.63 | 5.70 |
| 3 | 1.69 | 36.23 | 0.27 | 40.29 | 0.47 | 13.21 | 5.32 | 2.53 | 76.51 | 5.99 |
| 4 | 1.68 | 36.19 | 0.26 | 40.29 | 0.46 | 13.18 | 5.36 | 2.57 | 76.48 | 5.79 |
| 5 | 1.71 | 35.99 | 0.26 | 40.37 | 0.44 | 13.27 | 5.27 | 2.68 | 76.36 | 5.64 |
| 6 | 1.71 | 36.06 | 0.25 | 40.30 | 0.44 | 13.19 | 5.26 | 2.79 | 76.36 | 5.40 |
| 7 | 1.75 | 36.15 | 0.26 | 40.34 | 0.43 | 13.19 | 5.05 | 2.84 | 76.49 | 5.45 |
| 8 | 1.76 | 36.14 | 0.25 | 40.36 | 0.41 | 13.19 | 5.01 | 2.88 | 76.50 | 5.36 |
| 9 | 1.74 | 35.92 | 0.25 | 40.31 | 0.45 | 13.25 | 5.15 | 2.93 | 76.23 | 5.32 |
| 10 | 1.76 | 36.17 | 0.27 | 40.23 | 0.47 | 13.13 | 5.30 | 2.67 | 76.40 | 5.83 |
| 11 | 1.77 | 36.11 | 0.26 | 40.33 | 0.44 | 13.20 | 5.13 | 2.76 | 76.43 | 5.50 |
| 12 | 1.72 | 34.89 | 0.25 | 40.46 | 0.43 | 13.56 | 5.53 | 3.16 | 75.35 | 4.91 |
| 13 | 1.83 | 36.17 | 0.27 | 40.27 | 0.44 | 13.09 | 5.04 | 2.90 | 76.43 | 5.36 |
| 14 | 1.80 | 35.82 | 0.26 | 40.29 | 0.45 | 13.18 | 5.22 | 2.97 | 76.12 | 5.26 |
| 15 | 1.82 | 35.84 | 0.26 | 40.29 | 0.45 | 13.19 | 5.12 | 3.03 | 76.13 | 5.18 |
| 16 | 1.83 | 35.80 | 0.26 | 40.28 | 0.46 | 13.16 | 5.13 | 3.07 | 76.09 | 5.14 |
| 17 | 1.85 | 36.13 | 0.27 | 40.17 | 0.47 | 13.05 | 5.23 | 2.82 | 76.30 | 5.64 |
| 18 | 1.88 | 35.77 | 0.28 | 40.23 | 0.46 | 13.18 | 5.34 | 2.85 | 76.00 | 5.43 |
| 19 | 1.92 | 36.30 | 0.27 | 40.14 | 0.44 | 12.95 | 5.09 | 2.89 | 76.44 | 5.32 |
| 20 | 1.89 | 36.23 | 0.27 | 40.12 | 0.46 | 12.93 | 5.23 | 2.87 | 76.35 | 5.51 |
| 21 | 1.90 | 35.97 | 0.26 | 40.21 | 0.43 | 13.05 | 5.10 | 3.09 | 76.18 | 5.10 |
| 22 | 1.94 | 35.99 | 0.27 | 40.20 | 0.43 | 13.02 | 4.98 | 3.17 | 76.19 | 4.99 |
| 23 | 1.96 | 35.80 | 0.28 | 40.17 | 0.44 | 13.10 | 5.20 | 3.05 | 75.97 | 5.25 |
| 24 | 1.95 | 36.20 | 0.28 | 40.10 | 0.47 | 12.92 | 5.21 | 2.86 | 76.31 | 5.45 |
| 25 | 1.93 | 36.42 | 0.30 | 39.84 | 0.52 | 12.80 | 5.61 | 2.59 | 76.26 | 6.11 |
| 26 | 1.86 | 35.81 | 0.28 | 40.15 | 0.49 | 13.12 | 5.60 | 2.69 | 75.96 | 5.64 |
| 27 | 1.92 | 35.29 | 0.29 | 40.16 | 0.50 | 13.34 | 5.85 | 2.65 | 75.45 | 5.70 |
| 28 | 1.86 | 36.08 | 0.28 | 39.99 | 0.49 | 12.91 | 5.66 | 2.73 | 76.07 | 5.56 |
| 29 | 2.03 | 35.78 | 0.27 | 40.08 | 0.40 | 13.00 | 4.77 | 3.68 | 75.86 | 4.25 |
| 30 | 1.99 | 35.64 | 0.28 | 40.17 | 0.44 | 13.07 | 5.11 | 3.29 | 75.81 | 4.97 |
| 31 | 2.03 | 36.46 | 0.28 | 40.05 | 0.43 | 12.76 | 4.92 | 3.08 | 76.51 | 5.13 |
| 32 | 1.97 | 35.86 | 0.27 | 40.07 | 0.46 | 12.93 | 5.13 | 3.30 | 75.93 | 4.82 |
| 33 | 1.95 | 35.82 | 0.27 | 40.21 | 0.45 | 12.87 | 4.97 | 3.46 | 76.03 | 4.64 |
| 34 | 1.94 | 35.18 | 0.28 | 39.90 | 0.50 | 13.07 | 5.62 | 3.51 | 75.08 | 4.57 |
| 35 | 1.99 | 36.03 | 0.29 | 40.02 | 0.47 | 12.89 | 5.26 | 3.04 | 76.05 | 5.37 |
| 36 | 1.88 | 35.15 | 0.28 | 40.00 | 0.51 | 13.09 | 5.59 | 3.50 | 75.14 | 4.42 |
| 37 | 1.96 | 36.28 | 0.28 | 40.09 | 0.46 | 12.80 | 5.01 | 3.12 | 76.37 | 5.28 |
| 38 | 1.92 | 36.03 | 0.28 | 40.21 | 0.46 | 12.94 | 5.10 | 3.07 | 76.24 | 5.17 |
| 39 | 1.96 | 36.06 | 0.27 | 40.18 | 0.42 | 12.92 | 4.89 | 3.30 | 76.25 | 4.84 |
| 40 | 2.04 | 35.36 | 0.28 | 40.16 | 0.47 | 13.17 | 5.46 | 3.07 | 75.51 | 5.26 |
| 41 | 1.98 | 35.65 | 0.28 | 40.02 | 0.46 | 12.98 | 5.53 | 3.11 | 75.67 | 5.12 |
| 42 | 2.11 | 35.96 | 0.28 | 40.00 | 0.45 | 12.83 | 5.01 | 3.36 | 75.96 | 4.82 |
| 43 | 2.16 | 36.10 | 0.28 | 39.94 | 0.43 | 12.73 | 4.91 | 3.45 | 76.04 | 4.77 |
| 44 | 2.16 | 35.86 | 0.29 | 39.89 | 0.47 | 12.87 | 5.27 | 3.19 | 75.75 | 5.17 |
| 45 | 2.12 | 35.74 | 0.29 | 39.95 | 0.47 | 12.90 | 5.45 | 3.06 | 75.69 | 5.19 |
| 46 | 2.17 | 36.23 | 0.29 | 39.97 | 0.44 | 12.73 | 5.09 | 3.09 | 76.20 | 4.91 |
| 47 | 2.21 | 36.29 | 0.29 | 39.90 | 0.43 | 12.66 | 4.93 | 3.29 | 76.19 | 4.82 |
| Average | 1.90 | 35.93 | 0.27 | 40.15 | 0.45 | 13.04 | 5.21 | 3.03 | 76.09 | 5.23 |
| r.s.d. % | 7.49 | 0.93 | 4.77 | 0.37 | 5.66 | 1.39 | 4.59 | 9.43 | 0.48 | 7.76 |

Figure 8:
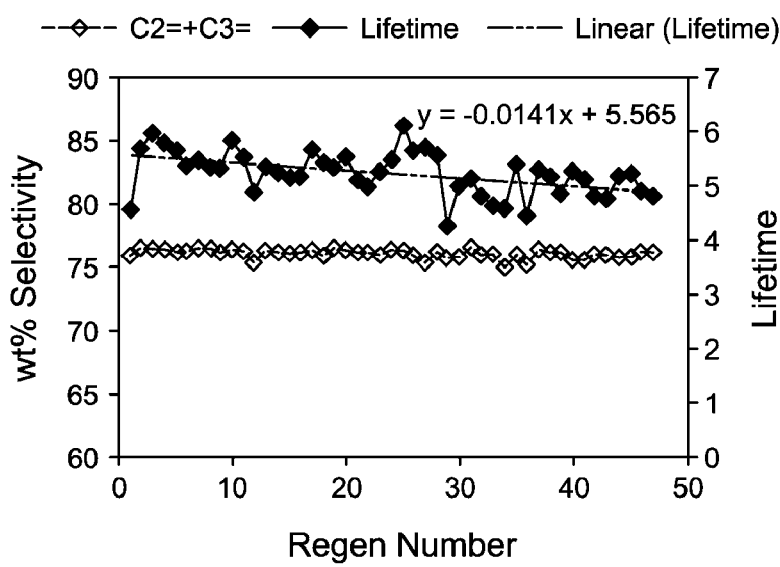
FIG. 8 shows catalyst lifetime and prime olefins selectivity after each regeneration cycle as a function of the number of regenerations in accordance with Example 3.

FIG. 8 presents prime olefins selectivity and catalyst lifetime after each regeneration step.

To compare regeneration at a temperature of 475° C. with conventional full regeneration at a high temperature of for example 650° C., we have compared fresh or fully regenerated catalyst with catalyst which has been regenerated at 650° C. "n" times after the 47 mild regenerations with n ranging from 1 to 5. The weight average selectivity was determined for fresh catalyst and the fully regenerated catalyst at the same conditions used to measure MTO performance of the mildly regenerated samples, namely 475° C., 172 kPag (25 psig) and 100 WHSV. The data are shown in the below Table 4 and Table 5. Note that the average prime olefin selectivity from the 47 mild regenerations was shown in Table 3 to be 76.09 wt %. The result is moderately better than that of a fresh catalyst, i.e., 75.07 wt % (Table 4), but is significantly better than the average prime olefins selectivity (73.16 wt %—average of the five runs shown in Table 5) of the spent catalyst that was fully regenerated at 650° C. after the 47 mild regenerations.

TABLE 4

Selectivity for fresh catalyst.

| Feed | $T_{reactor}$ (° C.) | WHSV ($hr^{-1}$) | C1 (wt %) | C2= (wt %) | C2° (wt %) | C3= (wt %) | C3° (wt %) | C4= (wt %) | C5+ (wt %) | Coke (wt %) | POS (wt %) | Lifetime (g/g) |
|---|---|---|---|---|---|---|---|---|---|---|---|---|
| Fresh MeOH | 475 | 100 | 1.75 | 36.50 | 0.26 | 38.57 | 0.58 | 12.70 | 7.21 | 2.42 | 75.07 | 17.08 |

TABLE 5

Selectivity for catalyst regenerated 47 + n times at 475° C.

| 47 + n | Feed | $T_{reactor}$ (° C.) | WHSV ($hr^{-1}$) | C1 (wt %) | C2= (wt %) | C2° (wt %) | C3= (wt %) | C3° (wt %) | C4= (wt %) | C5+ (wt %) | Coke (wt %) | POS (wt %) | Lifetime (g/g) |
|---|---|---|---|---|---|---|---|---|---|---|---|---|---|
| 1 | MeOH | 475 | 100 | 2.05 | 35.54 | 0.33 | 38.11 | 0.81 | 13.08 | 7.43 | 2.65 | 73.65 | 14.56 |
| 2 | MeOH | 475 | 100 | 2.08 | 35.35 | 0.32 | 37.96 | 0.76 | 12.89 | 7.25 | 3.39 | 73.31 | 13.10 |
| 3 | MeOH | 475 | 100 | 2.12 | 35.23 | 0.32 | 37.69 | 0.78 | 12.91 | 7.45 | 3.49 | 72.92 | 12.82 |
| 4 | MeOH | 475 | 100 | 2.21 | 35.52 | 0.33 | 37.56 | 0.80 | 12.80 | 7.52 | 3.26 | 73.08 | 13.27 |
| 5 | MeOH | 475 | 100 | 2.25 | 35.42 | 0.33 | 37.41 | 0.80 | 12.81 | 7.62 | 3.36 | 72.83 | 12.76 |

The principles and modes of operation have been described above with reference to various exemplary and preferred embodiments. As understood by those of skill in the art, the process described herein, as defined by the claims, encompasses other preferred embodiments not specifically enumerated herein.

Having described the various features of the method and apparatus, described in further numbered embodiments is:

1. A method of regenerating a molecular sieve catalyst for converting oxygenates into olefins, comprising:
   a) in a pretreatment stage, pretreating a molecular sieve catalyst under pretreatment conditions by heating the catalyst at a pretreatment temperature of between 320° C. to 700° C. in an oxygen depleted medium for a pretreatment residence time of between 1 minute to 2 hours, preferably between 1 minute to 1 hour; and
   b) in a regeneration stage, regenerating the catalyst under regeneration conditions by heating the catalyst at a regeneration temperature of between 200° C. to 700° C. in an oxidizing medium for a regeneration residence time of between 1 minute to 2 hours, preferably between 1 minute to 30 minutes.

2. The method of numbered embodiment 1, wherein in the regeneration stage, the pretreated catalyst is regenerated.

3. The method of numbered embodiment 1 or 2, wherein the pretreatment temperature is between 320° C. to 500° C., preferably between 350° C. to 480° C.

4. The method of any of the preceding numbered embodiments, wherein in the pretreatment stage the catalyst is heated at a first pretreatment temperature for a first residence time followed by increasing the temperature to a second pretreatment temperature and maintaining the second pretreatment temperature for a second residence time.

5. The method of numbered embodiment 4, wherein the first pretreatment temperature is between 320° C. to 480° C. and the second pretreatment temperature is between 400° C. to 700° C.

6. The method of any of numbered embodiments 4 or 5, wherein the pretreatment temperature is increased from the first pretreatment temperature to the second pretreatment temperature at a rate of between 5° C. to 50° C. per minute, preferably 10° C. to 20° C. per minute.

7. The method of any of numbered embodiments 1 to 6, wherein the temperature of the pretreatment stage is between 320° C. to 600° C. and the temperature in the regeneration stage is between 350° C. to 700° C.

8. The method of numbered embodiment 7, wherein the temperature of the pretreatment stage is between 320° C. to 400° C. and the temperature in the regeneration stage is between 400° C. to 480° C.

9. The method of any of the preceding numbered embodiments, wherein the catalyst in the pretreatment stage is heated by combustion of coke on the catalyst.

10. The method of any of the preceding numbered embodiments, wherein the catalyst in the pretreatment stage is heated by mixing the catalyst in the first stage with catalyst from the regeneration stage.

11. The method of any of the preceding numbered embodiments, wherein the oxygen depleted medium comprises less than 30%, preferably 20% or less, of the stoichiometric amount of oxygen for completely removing coke from the catalyst.

12. The method of any of the preceding numbered embodiments, wherein the method further comprises the step of controlling the pretreatment and/or regeneration stage conditions to control the amount of coke on the catalyst to between 0.05 to 1.0 wt % of coke on catalyst.

13. A method of regenerating a molecular sieve catalyst for converting oxygenates into olefins, comprising in a regeneration stage, regenerating the catalyst under regeneration conditions by heating the catalyst at a regeneration temperature of between 300° C. to 480° C. in an oxidizing medium for a regeneration residence time of between 1 to 30 minutes.

14. The method of any of the preceding numbered embodiments, wherein the oxidizing medium comprises at least a stoichiometric amount of oxygen for completely removing coke from the catalyst.

15. The method of any of the preceding numbered embodiments, wherein the method further comprises the step of feeding gaseous pretreatment effluent from the pretreatment stage to the regeneration stage.

16. A method for converting oxygenates into olefins by means of molecular sieve catalyst comprising:
   a) in a reaction stage, reacting a molecular sieve catalyst with the oxygenates under reaction conditions, the reaction conditions comprising a reaction temperature from 250° C. to 700° C., a pressure of 5 kPaa to 1 MPaa and a weight hourly space velocity of at least 1 $hr^{-1}$;
   b) regenerating at least a portion of the catalyst from the reaction stage as defined in any one of the preceding numbered embodiments; and
   c) returning the catalyst following regeneration to the reaction stage.

17. The method of numbered embodiment 16, wherein at least a portion of the catalyst is returned to the reaction stage following pretreatment in the pretreatment stage.

18. The method of any of the preceding numbered embodiments, wherein the catalyst comprises a silicoaluminophosphate molecular sieve.

19. A catalyst regeneration apparatus for an oxygenates-to-olefins conversion process, comprising:
   a) a catalyst pretreater for pretreating a molecular sieve catalyst under pretreatment conditions, said conditions comprising a temperature of between 320° C. to 700° C. in an oxygen depleted medium and a residence time of between 1 minute to 2 hours, preferably between 1 minute to 1 hour; and
   b) a regenerator for regenerating the catalyst in an oxidizing medium under regeneration conditions, said regeneration conditions comprising a temperature of between 200° C. to 700° C. and a residence time of between 1 minute to 2 hours, preferably between 1 minute to 30 minutes.

20. The apparatus of numbered embodiment 19, wherein in the pretreatment stage, the pretreater comprises a feed stream of catalyst from the regenerator to heat the catalyst in the pretreatment stage.

21. The apparatus of numbered embodiment 19 or 20, wherein in the pretreatement stage, the pretreater comprises combustion means for combusting coke on the catalyst to heat the catalyst in the pretreatment stage.

22. The apparatus according to any of numbered embodiments 19 to 21, wherein the apparatus further comprises a cooler for cooling the catalyst in the regenerator.

23. An oxygenates-to-olefins (OTO) conversion unit comprising an OTO reactor, a catalyst separator and a regeneration apparatus as defined in any one of numbered embodiments 19 to 22.

24. The unit according to numbered embodiment 23, wherein the catalyst reacts in the reactor with the oxygenates under reaction conditions, the reaction conditions comprising a reaction temperature from 250° C. to 700° C., a pressure of 5 kPaa to 1 MPaa and a weight hourly space velocity of at least 1 $hr^{-1}$; the regeneration apparatus regenerating at least a portion of the catalyst from the reactor; and the regeneration apparatus returning the catalyst following regeneration to the reactor.

25. The unit according to numbered embodiment 24, wherein the pretreater returns at least a portion of the catalyst to the reactor.

26. The method of numbered embodiment 16 or 17, comprising polymerizing said olefins in the presence of a polymerization catalyst.

What is claimed is:

1. A method of regenerating a molecular sieve catalyst for converting oxygenates into olefins, comprising:
   a) in a pretreatment stage, pretreating a molecular sieve catalyst under pretreatment conditions by heating the catalyst at a pretreatment temperature of between 300° C. to 700° C. in an oxygen depleted medium wherein in the pretreatment stage the catalyst is heated at a first pretreatment temperature for a first residence time of between 1 minute to 2 hours followed by increasing the temperature to a second pretreatment temperature and maintaining the second pretreatment temperature for a second residence time of between 1 minute to 2 hours, wherein the first pretreatment temperature is between 300° C. to 400° C. and the second pretreatment temperature is between 400° C. to 700° C., followed by cooling the catalyst to room temperature; and
   b) in a regeneration stage, regenerating the cooled catalyst under regeneration conditions by heating the catalyst at a regeneration temperature of between 350° C. to 500° C. in an oxidizing medium for a regeneration residence time of between 1 minute to 2 hours.

2. The method of claim 1, wherein the pretreatment temperature is increased from the first pretreatment temperature to the second pretreatment temperature at a rate of between 5° C. to 50° C. per minute.

3. The method of claim 1, wherein the catalyst in the pretreatment stage is heated by combustion of coke on the catalyst.

4. The method of claim 1, wherein the catalyst in the pretreatment stage is heated by mixing the catalyst in the first stage with catalyst from the regeneration stage.

5. The method of claim 1, wherein the oxygen depleted medium comprises less than 30% of the stoichiometric amount of oxygen for completely removing coke from the catalyst.

6. The method of claim 1, wherein the method further comprises the step of controlling the pretreatment and/or regeneration stage conditions to control the amount of coke on the catalyst to between 0.05 to 1.0 wt % of coke on catalyst.

7. The method of claim 1, wherein the oxidizing medium comprises at least a stoichiometric amount of oxygen for completely removing coke from the catalyst.

8. The method of claim 1, wherein the method further comprises the step of feeding gaseous pretreatment effluent from the pretreatment stage to the regeneration stage.

9. The method of claim 1, wherein the catalyst comprises a silicoaluminophosphate molecular sieve.

10. A method for converting oxygenates into olefins by means of molecular sieve catalyst comprising:
   a) in a reaction stage, reacting a molecular sieve catalyst with the oxygenates under reaction conditions, the reaction conditions comprising a reaction temperature from 320° C. to 700° C., a pressure of 5 kPaa to 1 MPaa and a weight hourly space velocity of at least 1 $hr^{-1}$;
   b) regenerating at least a portion of the catalyst from the reaction stage as defined in claim 1; and c) returning the catalyst following regeneration to the reaction stage.

11. The method of claim 10, wherein at least a portion of the catalyst is returned to the reaction stage following pretreatment in the pretreatment stage.

12. The method of claim 10 or 11, comprising polymerizing said olefins in the presence of a polymerization catalyst to form polymers.

* * * * *